United States Patent [19]
Nilsson et al.

[11] Patent Number: 5,015,576
[45] Date of Patent: * May 14, 1991

[54] MACROPOROUS PARTICLES FOR CELL CULTIVATION OR CHROMATOGRAPHY

[76] Inventors: Kjell Nilsson, Traktorgränden 4, S-222 51, Lund; Klaus H. Mosbach, Lackalänga 31-38, S-244 02, Furulund, both of Sweden

[ * ] Notice: The portion of the term of this patent subsequent to Jun. 19, 2007 has been disclaimed.

[21] Appl. No.: 114,421

[22] Filed: Oct. 28, 1987

Related U.S. Application Data

[63] Continuation-in-part of Ser. No. 919,325, Oct. 15, 1986, Pat. No. 4,935,365.

[30] Foreign Application Priority Data

Oct. 15, 1985 [SE] Sweden ............................. 85047645

[51] Int. Cl.⁵ ........................ C12P 21/08; C12P 1/00; C12N 11/02; C12N 5/00
[52] U.S. Cl. ................................. 435/70.21; 210/656; 210/660; 264/4.1; 264/4.6; 264/4.7; 435/41; 435/69.1; 435/71.1; 435/177; 435/178; 435/180; 435/182; 435/240.23; 435/240.24; 435/240.27; 435/803; 530/354; 935/59; 935/106
[58] Field of Search ................... 435/41, 69.1, 70.21, 435/71.1, 174, 175, 177, 178, 180, 182, 803, 240.23, 240.24, 240.27; 530/354; 106/122; 521/102; 264/49, 50, 4.1, 4.6, 4.7; 210/656, 660; 935/59, 106

[56] References Cited

U.S. PATENT DOCUMENTS

| 4,157,424 | 6/1979 | Boutle ........................... 264/49 X |
| 4,412,947 | 11/1983 | Cioca ................................ 260/123.7 |
| 4,500,358 | 2/1985 | Mayer et al. ..................... 264/50 X |
| 4,565,580 | 1/1986 | Miyata et al. ..................... 106/124 |
| 4,609,403 | 9/1986 | Wittmer et al. ................. 264/50 X |
| 4,647,536 | 3/1987 | Mosbach et al. ................. 435/177 |
| 4,798,786 | 1/1989 | Tice et al. .......................... 435/177 |
| 4,861,718 | 8/1989 | Dean, Jr. et al. .............. 435/174 X |
| 4,935,365 | 6/1990 | Nilsson et al. ..................... 435/178 |

FOREIGN PATENT DOCUMENTS

| 0025639 | 3/1981 | European Pat. Off. . |
| 0047064 | 3/1982 | European Pat. Off. . |
| 8200660 | 3/1982 | PCT Int'l Appl. ........... 435/240.24 |
| 8605811 | 10/1986 | PCT Int'l Appl. . |

Primary Examiner—David M. Naff
Attorney, Agent, or Firm—Poms, Smith, Lande & Rose

[57] ABSTRACT

Particles which enclose cavities can be produced by adding a water-insoluble solid, liquid or gaseous cavity generating compound to an aqueous solution of matrix material. Subsequent to forming particles by dispersion in a water-insoluble dispersion medium, the matrix is rendered insoluble in water by cooling, by covalent cross-linking or by polymerization. The cavity generating compound is washed out, whereafter the particles can be used as ion exchangers in gel filtration processes, in hydrophobic chromatography or in affinity chromatography, optionally subsequent to derivatizing the particles. The particles can also be used to advantage as microcarriers in the cultivation of anchorage-dependent cells.

7 Claims, 2 Drawing Sheets

MACROPOROUS PARTICLES FOR CELL CULTIVATION OR CHROMATOGRAPHY

This application is a continuation-in-part of application Ser. No. 06/919,325, filed Oct. 15, 1986, now U.S. Pat. No. 4,935,365.

BACKGROUND OF THE INVENTION

The separation of molecules is effected to a large extent with the aid of matrices which have connected thereto ligands which interact with the molecules concerned. These ligands may be ionic, hydrophobic or affinity ligands. Electrically neutral matrices of mutually different porosity are used when separating molecules in accordance with size as in gel filtration. These matrices are normally spheroidal in shape, in order to afford good flow properties. The flow properties of the separation system are also determined by the size of the particles present; the smaller the particle the higher the pressure drop, which results in a lower rate of flow. It is desirable in industrial applications to achieve high rates of flow, so that the molecules can be separated quickly. Another important parameter with regard to the particles used is the total specific surface area presented by the particles. The larger the specific surface area, the more quickly the molecules are able to penetrate the matrix and interact with the ligands. This specific surface area can be increased by reducing the sizes of the particles.

This antithesis is usually solved by taking a middle path, i.e. by using a relatively large particle size which is not optimum with regard to either the flow properties of the separation system or the specific surface area.

Animal cells have the capability to transform or produce complex compounds such as viral vaccines, immunochemicals, hormones or enzymes. The majority of animal cells are anchorage-dependent and thus demand a surface for their growth. Small beads (microcarriers) have been used to provide the necessary surfaces for anchorage-dependent cell growth.

Since the first use of these microcarriers for cell culture in 1976, a number of different materials have been employed for their preparation. These include dextran, gelatin, polystyrene and polyacrylamide and have, despite their different structures and composition all proven successful, to various extents, for cell culture. These microcarriers share, however, the common feature that only the surface area is utilized for cell growth, which implies a number of drawbacks. First, the cells are subjected to mechanical stress both by the mixing system in the reactor and by the motion of the beads in the medium. Second, in order to provide a large surface area the bead size has to be as small as possible. But, in order to achieve good growth a minimum number of cells are required on each bead. Thus, as the bead size decreases the number of cell doublings that can be achieved is reduced and a large number of transfers is required to reach the final production scale.

In order to increase the available surface area for cell growth, attempts have been made to provide porous microcarriers. It is known that macroporous matrices, e.g. collagen sponge, can be prepared by a freezing procedure, U.S. Pat. No. 4,412,947 (Chioca). The procedure involves dispersion/dissolution of collagen in dilute organic acid and a subsequent temperature reduction to −60° C. The frozen dispersion is thereafter freeze-dried. It is also known that particles of collagen are suitable for the culture of animal cells, U.S. Pat. No. 4,565,580 (Miyata et al.). It is also known that animal cells can be entrapped and cultivated in beads of collagen, U.S. Pat. No. 4,647,536 (Mosbach and Milsson). A collagen sponge, containing heavy particles for density increase, has also been used for the culture of animal cells, International Patent Application PCT/US86/00600 (Verax Corp.). However, the microsponge produced by this method will have a pore volume between 70 and 98%. Since the mechanical stability decreases as pore volume increases, it will be expected that such highly porous microsponges will have a limited stability. The method of producing these porous microsponges is quite specific for proteins (collagen) and to our knowledge this method has not been successfully used for other polymers like dextran, polyacrylamide, etc.

SUMMARY OF THE INVENTION

We, the inventors, have overcome the above problems with prior art matrixes by manufacturing particles which enclose a large number of cavities, so that the particles can be given a size which while enabling a high rate of flow through the particles, also presents a very large specific surface area which is desirable in separating molecules by chromatography. In addition to the separation of molecules, the extremely large surface area of the particles provided enables the particles to be used for cultivating anchorage dependent cells.

The present application describes a general method which is applicable for a wide variety of different water soluble polymers/monomers. As the method consists of a series of well defined physical operations it is also very well suited for industrial applications. It is also possible to carefully control the process and thereby predict the final properties of the final product.

The macroporous particles of the present invention are formed by dissolving the matrix forming material in an aqueous solvent and adding a water-insoluble dispersion medium or cavity generating compound to form a large number of cavities. The water-soluble matrix forming material is then made insoluble and separated out by cooling, by covalent cross-linking or by polymerization after being dispersed in an excess of water-insoluble dispersion medium. The cavity generating compound is then removed from the insoluble matrix material to provide the macroporous particles of the present invention.

Our method will produce beads with pore volumes ranging from a fraction of one or a few percent up to a maximum of 74%. The maximum pore volume which can be obtained is determined by the maximum amount of cavity generating compound which may be enclosed in a continuous matrix forming phase. Theoretical calculations shows that the maximum amount will be about 75%. However, pore volumes below 70% are preferred. The beads produced in this case have an optimal combination of pore volume and mechanical strength.

The above-described and many other features and attendant advantages of the present invention will become better understood by reference to the following detailed description when taken in conjunction with the accompanying drawings.

DESCRIPTION OF THE PREFERRED EMBODIMENTS

Figure 1:
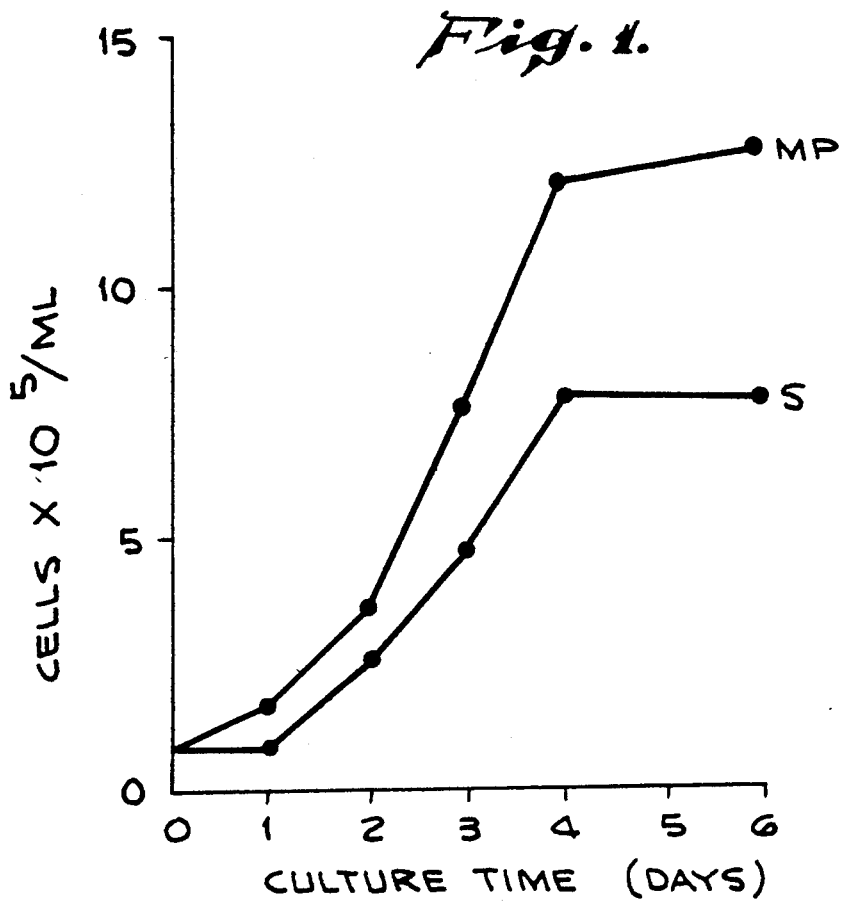
FIG. 1 is a graph showing test results of cell growth on the macroporous microcarriers of the present invention.

Macroporous beads of the present invention in which the anchorage-dependent cells have the possibility to utilize the interior surface, can be characterized as a semi-entrapment type bead, and will substantially minimize the problems associated with surface adsorbed cells. When compared to solid gelatin beads a reduction in the density is also obtained and thus results in a decrease in the power input necessary to keep the beads suspended.

These macroporous beads with a size of 10 to 500 micrometers, preferably about 200 micrometers, are produced by admixing a cavity generating compound with an aqueous solution of the matrix forming compound. The cavity generating compound may be solid, liquid or gaseous. The resultant mixture is then dispersed in a water-insoluble dispersion medium, to form particles therein. The matrix is then made insoluble in water by cooling the system, by-covalent cross-linking or by polymerization. Subsequent to the removal of the cavity generating compound, the resultant microsponge or macroporous particles can either be derivatized or used directly for their intended purposes. The cavities have a diameter of 1 to 50 micrometers, preferably about 10 to 20 micrometers.

The matrix forming compound is selected from proteins, polysaccharides or synthetic polymers. Examples of compounds which can be used are:
proteins—gelatin, albumin
polysaccharides—dextran, agarose
synthetic polymers—polyacrylamide.

An example of a solid cavity generating compound is calcium carbonate, which after the particles or beads have been produced by dispersing the mixture in a water-insoluble dispersion medium and the matrix has been made insoluble in water, can be removed by treating the system with an acid.

When the cavity generating compound used is in liquid form, it is necessary to add emulsifiers for stabilization. A water-soluble emulsifier (characterized by an HLB-value greater than 9). Droplets of cavity generating compound are formed by adding said compound containing a water-insoluble emulsifier (characterized by an HLB-value lower than 8) to the aqueous solution of the matrix continuously while stirring the system; the more vigorous the agitation the smaller the droplets formed.

When the cavity generating compound has been added in an amount sufficient to saturate the aqueous solution of matrix material, further addition will cause the matrix solution to form an excess of droplets of the cavity generating compound. By selecting emulsifiers which result in stable dispersions, particles of matrix material which contain droplets of the cavity generating compound are obtained, subsequent to rendering the matrix material insoluble in water. The cavity generating compound is then washed out with a solvent. The majority of organic solvents (water insoluble) can be used as the liquid cavity generating compound, as can also vegetable oils or mineral oils. Examples of suitable emulsifiers are Span 85, Arlacel 83 (water insoluble) and Tween 80, Triton X-100 (water soluble).

When the cavity generating compound used is in gas form, the gas is blown under high pressure through an aqueous solution of the matrix, which contains a water-soluble emulsifier, in order to generate stable gas bubbles in the system. The mixture is then dispersed in a water-insoluble dispersion medium, to obtain particles. A water-insoluble emulsifying agent is also added to the dispersion medium, in order to obtain a stable dispersion. The emulsifiers and dispersion medium are removed subsequent to rendering the particles insoluble in water.

EXAMPLE 1

Thermal gelatin (liquid cavity generating compound).

Gelatin was dissolved by heating the same in water to a concentration of 10% w/v. 6 g of emulsifier (Tween 80) were added to 100 ml of the gelatin solution. 500 ml of toluene containing 30 g emulsifier (Span 85) were then stirred into the solution. When beads of the desired size had formed, the dispersion was cooled to a temperature beneath the solidification temperature of the gelatin. The afore-described process results in the formation of gelatin beads which are saturated with droplets of toluene. These toluene droplets can be removed by washing the beads with ethanol and acetone, therewith providing a gelatin bead which is filled with cavities.

The gelatin beads can then be cross-linked with, for example, glutaraldehyde, in order to further increase stability.

EXAMPLE 2

Thermal gelatin (gaseous cavity generating compound).

5 g of emulsifier (Triton x-100) were added to 100 ml of gelatin solution (10% w/v). Air under high pressure was then blown through the solution, to form a large number of air bubbles therein. Beads were formed by dispersing the solution in 500 ml toluene/chloroform (73/27, w/v) containing 30 g emulsifier (Span 85), while stirring the system. Subsequent to obtaining beads of the desired size, the dispersion was cooled, so as to solidity the gelatin. The organic solvents were then removed, by washing with ethanol and acetone. The resultant beads can then be cross-linked further with, for example, glutaraldehyde.

EXAMPLE 3

Thermal gelatin (solid cavity generating compound).

10 g of calcium carbonate were added to 100 ml of gelatin solution (10% w/v), whereafter beads were produced in accordance with Example 1. The beads were treated with acid, so as to dissolve the calcium carbonate and therewith form cavities in the beads.

EXAMPLE 4

Polymerization.

Acrylamid (17 g) and bisacrylamide (1.2 g) were dissolved in a Tris-buffer (100 ml, 0.05M, pH 7). Ammonium persulphate (0.5 g/ml, 0.25 ml) and emulsifier (Triton x-100, 6 g) were added to the monomer solution. 500 ml of toluene containing an emulsifier (Span 85, 30 g) were then stirred into the system. The organic solvents were washed out with ethanol and acetone, upon termination of the polymerization process.

EXAMPLE 5

Covalent cross-linking.

Sodium hydroxide (0.7 g) and emulsifier (Tween 80, 6 g) were added to an aqueous solution of dextran (10%, w/v, 100 ml). Toluene (500 ml) having an emulsifier (Span 85, 30 g) and epichlorohydrin (1.5 g) dissolved therein was then added to the solution while stirring the system. The temperature of the system was raised to 40° C. over a period of 2 hours, and then to 70° C. over a further period of 12 hours. The resultant beads were washing with ethanol and acetone, in order to remove organic solvent. The properties of the beads formed can be varied, by varying the quantity of dextran and the quantity of epichlorohydrin used.

EXAMPLE 6

Covalent cross-linking.

Chitosan was dissolved in formic acid (5%, w/v) to a concentration of 30 g/l. 100 ml of solution were admixed with emulsifier (Tween 80, 6 g) and, while stirring the system, with toluene (500 ml) containing an emulsifier (Span 85, 30 g. Subsequent to obtaining beads of the desired size, formaldehyde (20 ml) was added to the system. The resultant beads were washed with methanol after a time lapse of one hour.

EXAMPLE 7

Preparation of macroporous gelatin beads for cell culture.

Gelatin was dissolved in water at a concentration of 8% (w/v) and kept at 60° C. To 100 ml solution containing Tween 80 (Atlas Chemie, 6% w/v) was continuously added toluene containing SPAN 85 (Atlas Chemie, 6% w/v). The added toluene formed droplets in the gelatin solution until saturation with the droplet size depending on the mixing speed. Through addition of excess toluene to a final volume of 400 ml beads of gelatin containing droplets of toluene were produced. After cooling the dispersion below 20° C. 200 ml ethanol was added. The formed beads were then further washed with ethanol and after a final wash with acetone dried overnight at room temperature. The dry beads were sieved and in order to increase the mechanical strength of the beads the fraction between 125 and 180 micrometers further was cross-linked with glutaraldehyde (8.8% w/v) by treating for 30 minutes at 15° C. after reswelling in 0.1 M phosphate buffer with pH 7.0. After removal of excess glutaraldehyde the beads were heat treated at 121° C. for 20 minutes, which reduced the volume to about 50%, and after washing with water and acetone finally dried overnight at 60° C.

EXAMPLE 8

Comparison of cell growth on solid gelatin beads (made according to Nilsson, K. and Mosbach, K. 1980. Preparation of immobilized animal cells. FEBS Lett. 118:145–150) and on macroporous beads or microcarriers according to Example 7.

Both types of beads were autoclaved in PBS (phosphate buffered saline) and equilibrated with culture medium (DMEM, 10% FCS 50 g/ml gentamycin, 4 mM glutamine). BHK-cells, routinely maintained in plastic flasks, were trypsinized and mixed with the beads (1 ml) at a concentration of 95,000 cells/ml in a spinner bottle to a final volume of 50 ml. The mixture was incubated at 37° C. in an atmosphere of 95% air/5% $CO_2$. Beginning on the second day, 40 ml of medium was exchanged daily.

Both types of beads (1 ml) and Vero-cells were mixed in 20 ml of growth medium to a final cell concentration of 160,000 cells/ml. After one day of culture the medium volume was adjusted to a final volume of 50 ml. Beginning on the second day, 40 ml medium was exchanged daily. For determination of cell growth duplicate samples of 0.5 ml were taken from the suspension of beads. After sedimentation of the beads, 0.3 ml supernatant was removed and 0.8 ml Dispass (Bochringer, grade 11, 5 mg/ml in PBS) was added. The mixture was incubated at 37° C. until the beads were dissolved (about 30 min) after which the cells were counted.

Figure 2:
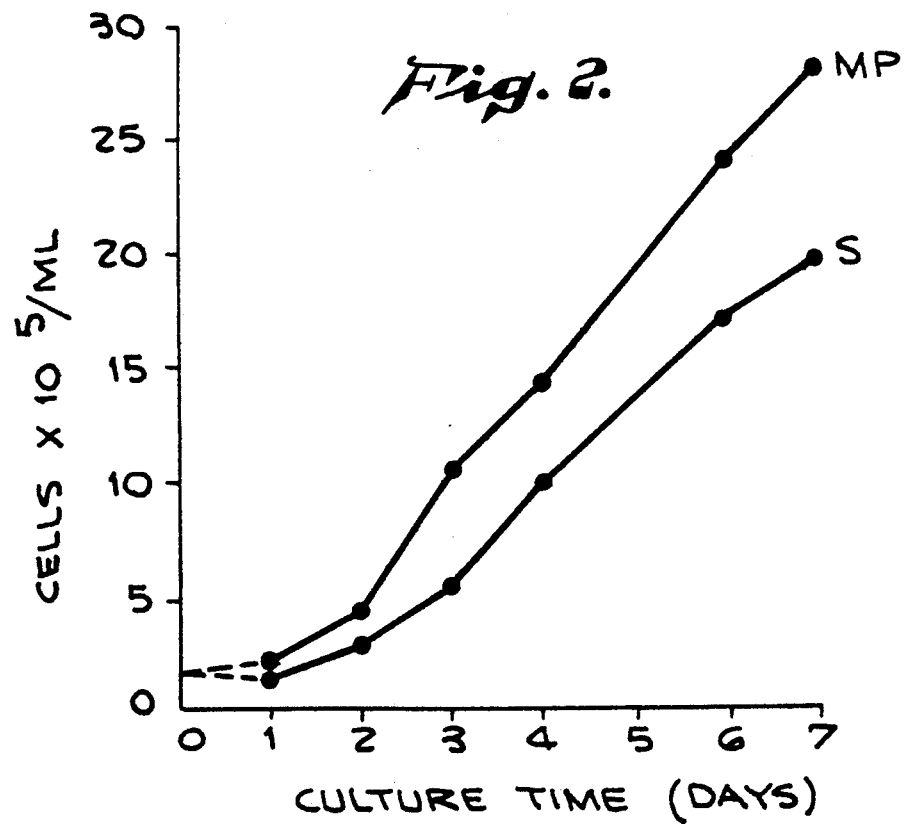
FIG. 2 is another graph showing test results of cell growth on the macroporous microcarriers of the present invention.

The capability to support the growth of two cell lines, Baby Hamster Kidney cells (BHK) and African green monkey cells (VERO) on macroporous cells (MP) compared favorably to solid gelatin beads (S), see FIGS. 1 and 2. In both cases, almost twice as many cells were obtained on the porous beads of Example 7. In addition, a higher number of cells attached to the porous beads from the inoculation due to the more favorable conditions for attachment caused by the cavities. In this case, only 2% (v/v) microcarriers were used and therefore the final cell yield should be limited by the available surface area. However, the final cell yield of Vero-cells is not obtained after a growth period of 7 days after which, despite frequent medium exchanges, the culture medium starts to be insufficient for further growth. As normally a concentration of 10% (v/v) microcarriers (solid) is used, a perfusion system is necessary in order to fully exploit the possibilities of these macroporous microcarriers.

This semi-entrapment gives increased stability to the normally fragile animal cells, allows for high cell densities within the beads and makes the preparations suitable for continuous operation.

EXAMPLE 9

Growth of vero cells at different initial cell concentrations were measured. Macroporous gelatin beads (2 ml) prepared according to Example 7 and VERO cells were mixed at different cell concentration in 25 ml of growth medium. At day one the medium volume was adjusted to 50 ml.

In all the examples the sizes of the beads could be varied between 10 and 500 micrometers, e.g. 50, 100, 250, 400 etc. and the cavity volume between 1 and 75%, such as 20, 40, 60, 70% etc.

Figure 3:
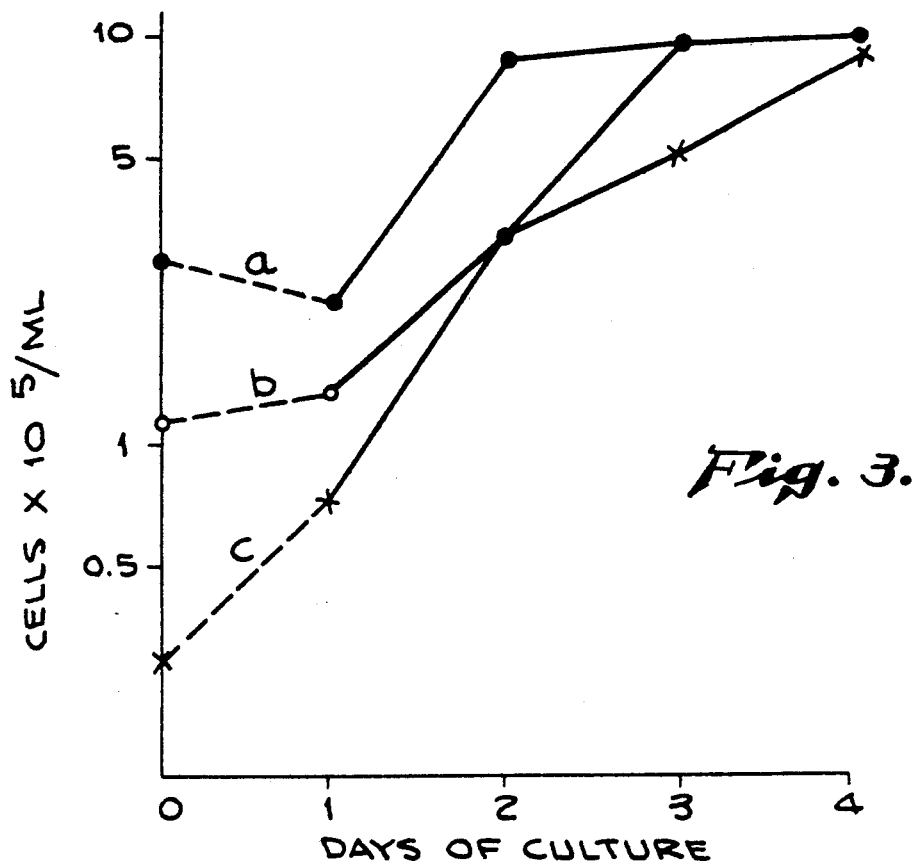
FIG. 3 is an additional graph showing test results regarding growth of cells at different concentrations on the microcarriers of the present invention.

FIG. 3 shows an initial cell concentration of 280,000 cells/ml, 122,000 cells/ml and 28,000 cells/ml.

The graph shows that with our porous microcarriers it is possible to reduce the initial cell concentration and still obtain the same final cell yield. This is due to the fact that larger beads can be used without any limitations in available surface area. At the start each bead has to be provided with a minimum number of cells (usually 5–10 cells/bead) as the cells usually are not transferred between the beads. By using larger beads the number of beads are reduced and consequently the required initial cell amount is reduced.

The microcarriers of the present invention are especially well suited for use in bioreactors for the growth of anchorage-dependent cells. The reactors typically have volumes of 0.1 to 20 liters. Any of the conventional procedures used in the prior art for immobilizing such organisms on microcarriers can be used in the present invention including such techniques as adsorption and chemical coupling. For example, in the case of certain organisms it will only be necessary to mix the microcarriers of the present invention in a medium inoculated with the specific organism. After a short period of time, the organism will colonize the microcarriers and become entrapped in their pores. In the case of some organisms such as fibroblasts and hybridomas, it also may be desirable to coat the microcarriers with attachment-promoting materials such as fibronectin, polylysine and anti-hybridoma antibodies prior to inoculation. Other techniques, such as applying a net charge to the surface of the microcarrier can also be used to enhance immobilization.

Any of the known procedures can be used for bringing the immobilized bioactive material into direct contact with a liquid reagent stream such as a growth supporting medium for culturing of immobilized organisms. Any of the numerous arrangements available in the prior art including such well-known apparatus as stirred tank reactors, fixed bed reactors, fluidized bed reactors, moving bed reactors, tricle reactors and the like can be used. Generally, when culturing organisms the microcarriers are charged to a suitable reactor and mixed therein with a nutrient medium and an inoculum of the organism. The microcarriers should be completely submerged. The microcarriers are incubated so that the organisms grow and colonize within the porous matrix of the microsponge. Fresh nutrient media along with other materials necessary for growth, such as oxygen in the case of aerobic organisms, are supplied in a continuous manner to the reactor and harvest liquor containing the biochemical product of interest is recovered. The biochemical product may comprise a primary or secondary metabolite of an immobilized organism, excess biomass generated by an immobilized organism containing for example a non-secretory product, an immobilized enzyme catalyzed reaction product or the like.

The microcarriers can be used in mixed or motive reactor systems wherein motion is imparted to the microcarriers during cell growth. The microcarriers should be weighted when they are used in such motive reactor systems. The microcarriers should be weighted so that the specific gravity is above 1.0. Specific gravities between 1.5 and 2.0 are preferred. The additives can be any of the weighted additives disclosed in PCT application No. 86/05811 (Published Oct. 9, 1986), the contents of which is hereby incorporated by reference. The weighted additives include chromium, tungsten, molybdenum, cobalt, nickel, titanium and their alloys. The weighted additives are preferably incorporated into the water-soluble polymer as a finely divided powder having particle sizes on the order of 10 to 40 microns.

Figure 4:
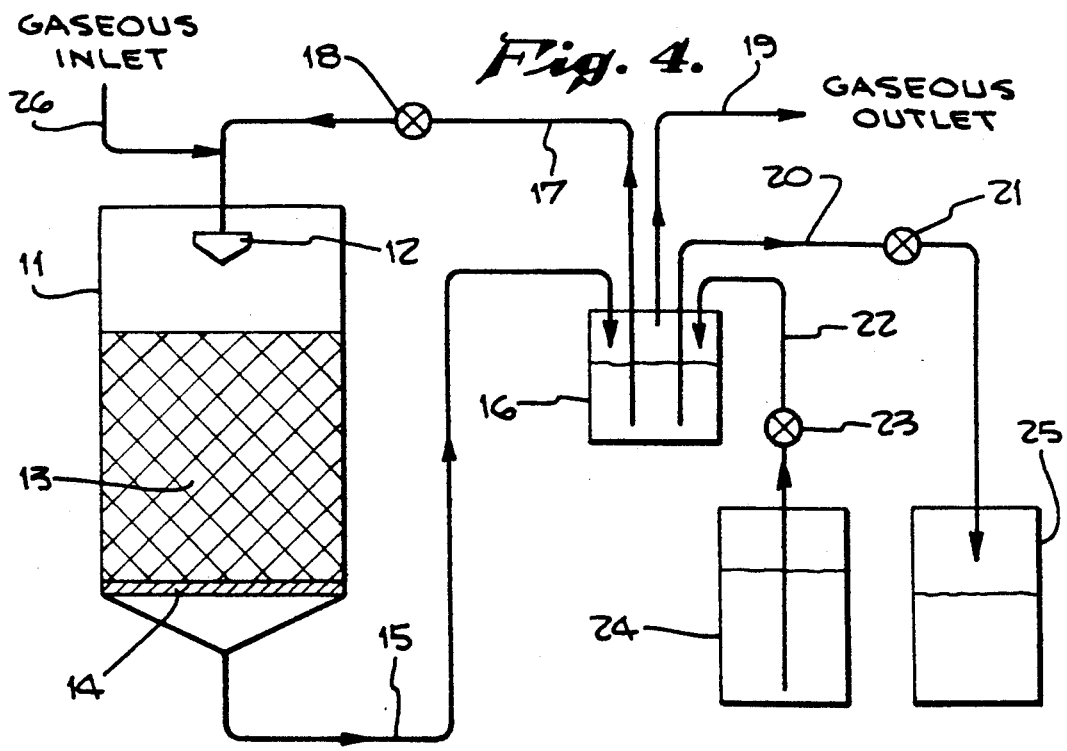
FIG. 4 is a schematic representation of an exemplary tricle-bed bioreactor system for use with the macroporous microcarriers of the present invention.

An exemplary tricle cell reactor system in which our microcarriers can be used is shown in FIG. 4. The microcarriers are packed into the reactor 11 where they are supported by conventional support structures 13 and 14. Growth media is continually perfused through the reactor by way of spray nozzle 12. The growth media flow rate to the nozzle 12 through line 17 is controlled by valve 18. Gases, such as oxygen, are introduced through line 26 if necessary for cell growth.

The growth medium is sprayed over the microcarrier bed and forms a thin film which covers the microcarriers. This thin film together with a large surface area provides an efficient mass transfer, both for gases (e.g. oxygen) and for nutrients. After passing the reactor, the media, now containing cellular product, is fed into a regulation reservoir 16 via line 15. In the reservoir 16, important parameters like pH are controlled. The reservoir 16 is continuously perfused with new media from media tank 24 via valve 23 and line 22. Media which contains product is withdrawn through line 20 as controlled by valve 21 into product reservoir 25. Gaseous by-products are removed through outlet 19. This system is well suited for growing a wide variety of animal cells and organisms including the production of monoclonal antibodies using hybridoma anchored to the microcarriers. Genetically engineered microbial cells can also be grown which secrete desirable protein products.

An advantage of a tricle bed reactor over conventional bioreactors (stirred tanks, packed beds, fluidized beds, etc.) is that the tricle bed reactor does not have to be filled with medium. However, it has not been possible to use tricle bed reactors for cell culture before due to the lack of a suitable packing material. The packing material must exhibit the following properties:

a. Enough mechanical strength in order not to be compressed.
b. Relatively large bead size to prevent bridging of cells between different beads which will cause channeling of the media flow.
c. Large surface area. To provide efficient mass transfer a large surface area is necessary. By using solid beads this can only be accomplished through a size reduction which will be contrary to requirement b.
d. Water swellable matrix. The matrix must be able to swell in and retain water. If not, the gas flow will cause the particles to become partly dry and thereby dehydrate the immobilized cells.

The microcarriers of the present invention are suitable to use in tricle bed reactors due to the following reasons:

a. Pore volumes below 75% (preferably 50–70%) makes the mechanical strength high enough to withstand compression.
b. Large bead sizes can be used while still maintaining a high surface area due to the porosity.
c. The materials employed for their preparation, i.e. proteins, polysaccharide or water-swellable polymers are all able to swell in and retain water.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but are only limited by the following claims.

We claim:

1. A method for using macroporous particles in a bioreactor system for producing a biochemical product, said method comprising the steps of:
    dissolving a water-soluble matrix material in an aqueous solvent to form an aqueous solution comprising said matrix material dissolved in said aqueous solvent;
    mixing a sufficient amount of a water-insoluble liquid cavity generating compound with said aqueous solution of matrix material to form a dispersion of droplets of said liquid cavity generating compound in said aqueous solution;
    adding additional liquid cavity generating compound to said dispersion in an amount sufficient to saturate said dispersion and form droplets of said dispersion dispersed in said liquid cavity generating compound;

solidifying said dispersed droplets to form beads of said matrix material having a large number of pores containing said liquid cavity generating compound dispersed therethrough;

separating said solidified beads from said liquid cavity generating compound;

removing said liquid cavity generating compound from the pores of said beads to form macroporous particles having a particle size of between about 10 to 500 micrometers and a large number of pores having diameters of between about 1-50 micrometers;

immobilizing an organism on said macroporous particles to produce an immobilized organism, said organism capable of producing said biochemical product;

charging said bioreactor system with said immobilized organism;

contacting said immobilized organism with a liquid reagent stream for culturing said immobilized organism; and recovering said biochemical product from said bioreactor system.

2. A method for using macroporous particles according to claim 1 wherein said bioreactor system is charged with between about 0.1 to 20 liters of said immobilized organism.

3. A method according to claim 1 wherein said organism is a hybridoma and said biochemical product comprises monoclonal antibodies.

4. A method according to claim 1 wherein said organism is an animal cell and said biochemical product comprises animal cell products.

5. A method according to claim 1 wherein said organism is a genetically engineered microbial cell and said biochemical product comprises secreted protein products.

6. A method for using macroporous particles as microcarriers for culturing anchorage-dependent animal cells comprising the steps of:

dissolving a water-soluble matrix material in an aqueous solvent to form an aqueous solution comprising said matrix material dissolved in said aqueous solvent;

mixing a sufficient amount of a water-insoluble liquid cavity generating compound with said aqueous solution of matrix material to form a dispersion of droplets of said liquid cavity generating compound in said aqueous solution;

adding additional liquid cavity generating compound to said dispersion in an amount sufficient to saturate said dispersion and form droplets of said dispersion dispersed in said liquid cavity generating compound;

solidifying said dispersed droplets to form beads of said matrix material having a large number of pores containing said liquid cavity generating compound dispersed therethrough;

separating said solidified beads from said liquid cavity generating compound;

removing said liquid cavity generating compound from the pores of said beads to form macroporous particles having a particle size of between about 10 to 500 micrometers and a large number of pores having diameters of between about 1-50 micrometers;

mixing said macroporous particles with a growth medium and an animal cell line to form a growth support medium;

incubating said growth support medium to promote cell attachment and growth; and recovering said cells from said macroporous particles.

7. A method for using macroporous particles as ion-exchangers in chromatography, said method comprising the steps of:

dissolving a water-soluble matrix material in an aqueous solvent to form an aqueous solution comprising said matrix material dissolved in said aqueous solvent;

mixing a sufficient amount of water-insoluble liquid cavity generating compound with said aqueous solution of matrix material to form a dispersion of droplets of said liquid cavity generating compound in said aqueous solution;

adding additional liquid cavity generating compound to said dispersion in an amount sufficient to saturate said dispersion and form droplets of said dispersion dispersed in said liquid cavity generating compound;

solidifying said dispersed droplets to form beads of said matrix material having a large number of pores containing said liquid cavity generating compound dispersed therethrough;

separating said solidified beads from said liquid cavity generating compound; and removing said liquid cavity generating compound from the pores of said beads to form said macroporous particles having a particle size of between about 10 to 500 micrometers and a large number of pores having diameters of between about 1-50 micrometers;

derivatizing said macroporous particles to form derivatized macroporous particles having ion-exchange groups;

preparing chromatography columns packed with said derivatized macroporous particles; and using said chromatography columns for ion-exchange chromatography.

* * * * *